United States Patent [19]

Ooshima et al.

[11] Patent Number: 5,206,007

[45] Date of Patent: Apr. 27, 1993

[54] ANTI-HUMAN MYOCARDIAL C PROTEIN MONOCLONAL ANTIBODY AND HYBRIDOMA PRODUCING THE ANTIBODY

[75] Inventors: Akira Ooshima, Wakayama; Toshiro Yamaguchi, Chiba, both of Japan

[73] Assignee: Daiichi Radioisotope Laboratories, Ltd., Tokyo, Japan

[21] Appl. No.: 633,677

[22] Filed: Dec. 26, 1990

[30] Foreign Application Priority Data

Dec. 27, 1989 [JP] Japan ................... 1-339082

[51] Int. Cl.$^5$ ............ A61K 49/00; C12N 5/12; C07K 15/28
[52] U.S. Cl. ................... 424/9; 435/240.27; 530/388.1
[58] Field of Search ............ 530/387, 388.1; 435/240.27, 70.21; 436/548; 424/9, 1.1, 85.8

[56] References Cited

U.S. PATENT DOCUMENTS 4,943,427 7/1990 Yazaki et al. ............ 424/1.1

FOREIGN PATENT DOCUMENTS 268707 6/1988 European Pat. Off. .

OTHER PUBLICATIONS

Kawashima et al., *J. Biochem.*, 99, 1037–1047 (1986).

Primary Examiner—David L. Lacey
Assistant Examiner—Susan L. Futrovsky
Attorney, Agent, or Firm—Bacon & Thomas

[57] ABSTRACT

Disclosed herein is an anti-human myocardial C protein monoclonal antibody which is specific to human myocardial C protein and a hybridoma producing the monoclonal antibody. The monoclonal antibody of this invention is useful as a drug for the image diagnosis of heart diseases, when labelled with an enzyme, radioisotope or a fluorescent substance.

5 Claims, 3 Drawing Sheets

ANTI-HUMAN MYOCARDIAL C PROTEIN MONOCLONAL ANTIBODY AND HYBRIDOMA PRODUCING THE ANTIBODY

BACKGROUND OF THE INVENTION i) Field of the Invention

This invention relates to an anti-human myocardial C protein monoclonal antibody, a hybridoma producing the antibody, process for preparing the monoclonal antibody and a drug for the diagnosis of heart diseases using the monoclonal antibody.

ii) Description of the Background Art

Image diagnosis plays an important role in diagonosing ischemic heart diseases typified by myocardial infarction, making it possible to non-invasively identify the region where myocardial necroses occur and the seriousness of the disease. Among the image diagnoses is scintiscanning which utilizes a monoclonal antibody against human myocardial myosin.

Another approach for diagnosing ischemic heart diseases has also been proposed, where the amount of myosin is measured which flowed out of the myocardial cell membrane due to necroses of the myocardial tissue.

Human myocardial C protein is a protein which constitutes human myocardial cells and is associated with the heavy chain of human myocardial myosin. It has a molecular weight from 135,000 to 150,000, which mediates between the heavy chain of human myocardial myosin (MW: 450,000~480,000) and the light chain of human myocardial myosin (MW: 70,000~80,000). In the diagnosis of myocardiopathy, measurement of human myocardial C protein also provides useful clinical information.

Conventionally, no anti-human myocardial C protein monoclonal antibody has been established which is usable in the diagnosis of myocardiopathy.

SUMMARY OF THE INVENTION

An object of the invention is to provide an anti-human myocardial C protein monoclonal antibody.

Another object of the invention is to provide a hybridoma which produces the monoclonal antibody.

A further object of the invention is to provide a process for preparing the monoclonal antibody.

A further object of the invention is to provide a drug for the diagnosis of human heart diseases.

DETAILED DESCRIPTION OF THE INVENTION AND PREFERRED EMBODIMENTS

Figure 1:
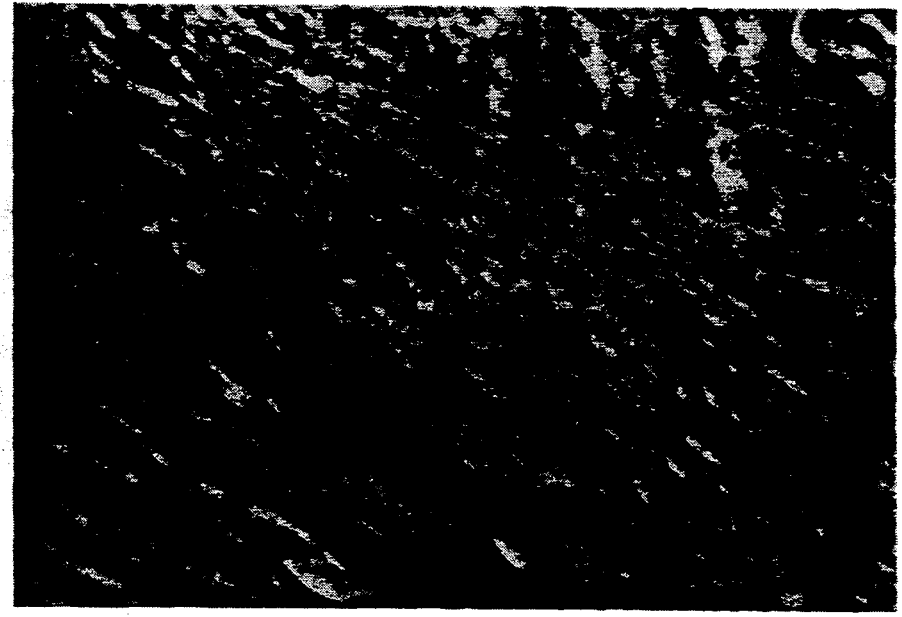
FIG. 1 is a photograph showing a tissue slice of human old myocardial infarction (stained with hematoxiline. eosine) used in Example 3.
Figure 2:
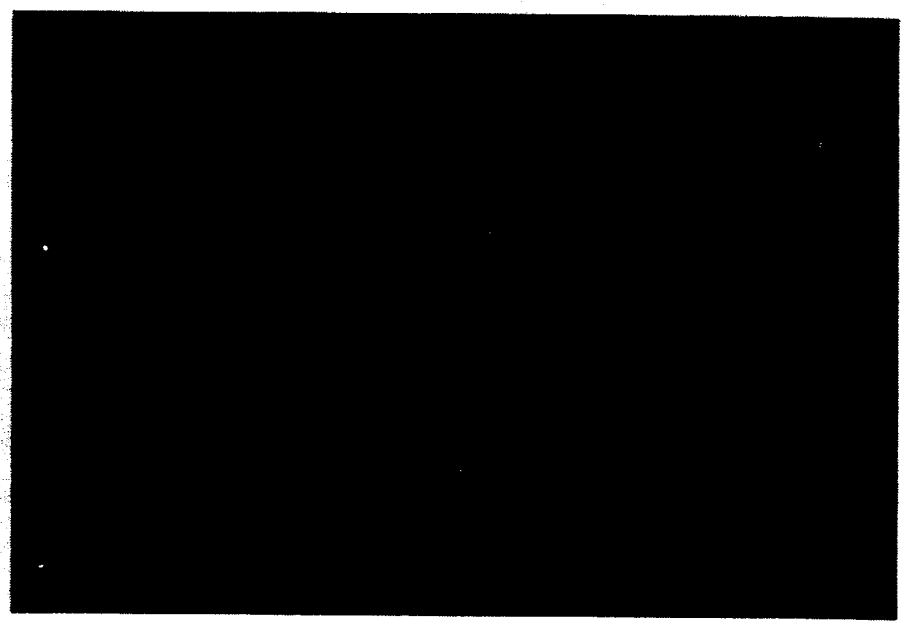
FIG. 2 is a photograph showing a tissue slice of human old myocardial infarction observed by way of indirect fluorescent antibody technique using anti-human myocardial C protein monoclonal antibody of this invention.
Figure 3:
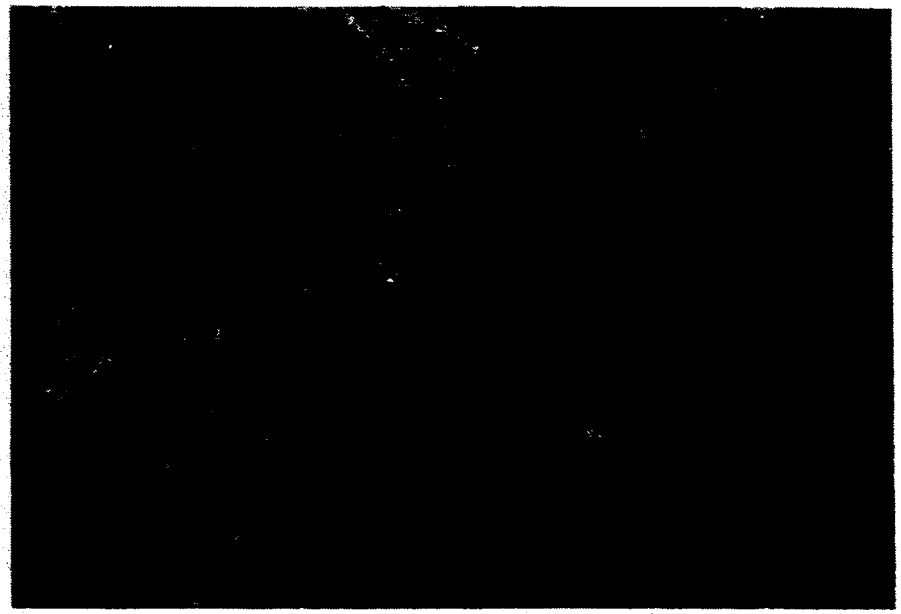
FIG. 3 is a photograph showing a tissue slice of rabbit ischemic myocardiopathy (stained with hematoxiline. eosine) used in Example 4.
Figure 4:
FIG. 4 is a photograph showing a tissue slice of rabbit ischemic myocardiopathy administered with anti-human myocardial C protein monoclonal antibody of Example 4, which is observed by way of direct fluorescent antibody technique.
Figure 5:
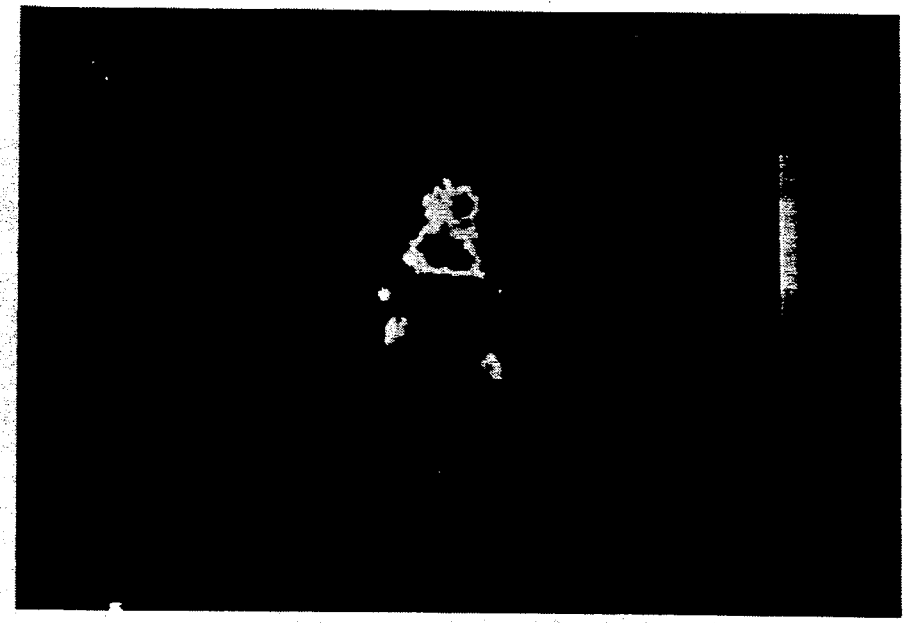
FIG. 5 is a photograph taken with a gamma camera showing the anterior imaging of a rabbit suffered from ischemic myocardiopathy, administered with $^{111}$In-antihuman myocardial C protein monoclonal antibody—DTPA of Example 8.
Figure 6:
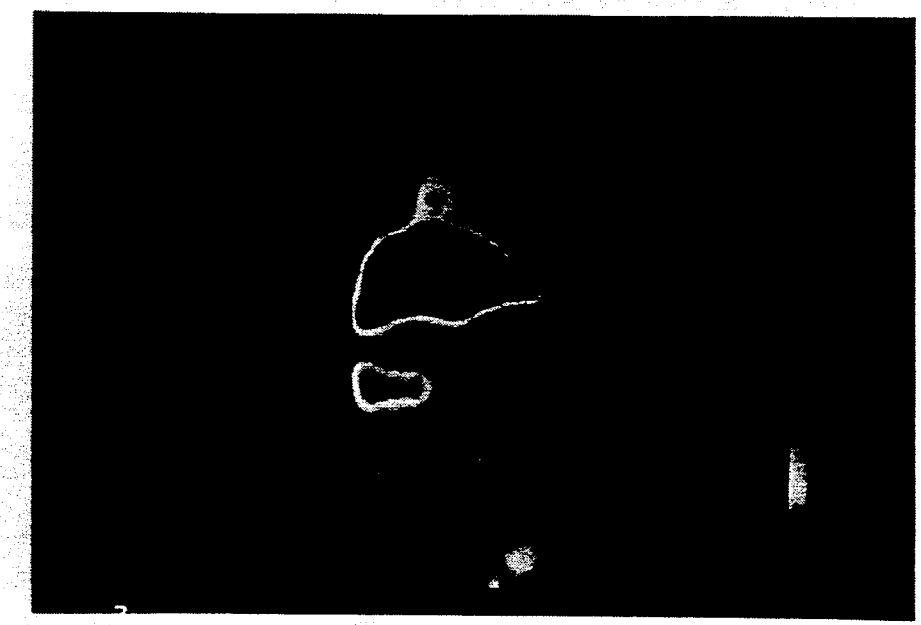
FIG. 6 is a photograph taken with a gamma camera showing the anterior imaging of a rabbit suffered from ischemic myocardiopathy, administered with $^{99m}$Tc-antihuman myocardial C protein monoclonal antibody—DTPA of Example 10.

The monoclonal antibody of this invention is prepared, for example, by collecting myeloma cells and antibody-producing cells from an animal immuned with human myocardial C protein; fusing them to obtain hybridomas; allowing the hybridomas to propagate in the abdominal cavity of an animal or in a culture broth; collecting monoclonal antibodies from the ascites or from the culture broth.

The human myocardial C protein to be used as the antigen in the present invention is prepared, for example, by using the human heart muscle as a starting material, purifying the crude myosin, obtaining a target C protein band by SDS-PAGE method therefrom and extracting out from the gel. This procedure is basically described in Biochem. J., K. M. Prince, 191, 571–580(1980).

The hybridomas which produce the monoclonal antibody of the present invention are prepared by a so-called cell fusion process, wherein antibody-producing cells are obtained from an animal immuned with the mentioned human myocardial C protein, allowing the cells to fuse with myeloma cells, selectively propagating the obtained hybridomas, searching antibody-producing hybridomas among them and cloning to obtain monoclonal antibody-producing hybridomas.

As the antibody-producing cells, mention may be given to spleen cells, lymph node cells, B-lymphocytes. They are obtainable from animals immuned, for example, with human myocardial C protein or with an antigen prepared from the protein. Animals to be immuned include mice, rats, rabbits, goats and horses. Immunization is carried out, for example, by giving an animal human myocardial C protein as it is or as a mixture with complete Freund's adjuvant, subcutaneously, intramuscularly or intraperitonealy, once or twice a month, about 50 micro grams/200 micro liters each time, for 2 to 4 months. Isolation of the antibody-producing cells are performed by collecting them from the immuned animal 2 to 4 days after the last immunization.

Myeloma cells usable in this invention are those derived from animals including mice, rats, and the human. It is advisable that the antibody-producing cells and myeloma cells are from animals of the same species.

The cell fusion is performed, for example, by following a known method according to Koehler and Milstein (Koehler, G. and Milstein, C., Nature, 256, 495(1975)) or a modified method of it. Very briefly, the cell fusion is performed by blending antibody-producing cells and myeloma cells in a culture medium such as RPMI 1640. In this process, it is advisable to add a fusion accelerator such as polyethylene glycol.

After the cell fusion is completed, a culture medium such as RPMI 1640 is added for dilution, followed by centrifugal separation. The sediment is suspended in a selective culture medium such as HAT Medium, and cultured for selecting hybridomas. Subsequently, the supernatant of the culture is used for searching the antibody-producing hybridoma by way of enzyme antibody technique, then cloning is carried out by way of the limiting dilution technique to obtain hybridomas which produce the monoclonal antibody of the present invention.

The present inventors thus prepared hybridomas which produce monoclonal antibodies specific to human myocardial C protein, and deposited them with the Fermentation Research Institute, Agency of Industrial Science and Technology Ministry of International Trade and Industry, 1-3, Higashi 1-chome, Tsukuba-shi, Ibaraki-ken 305, Japan, on Jun. 14, 1989 as FERM BP-2473. The monoclonal antibody of this invention can be prepared by using this hybridoma.

To produce the monoclonal antibody of this invention, the above-explained hybridoma is cultured in a suitable culture broth or in a living body, and the monoclonal antibodies are collected from the culture. For culturing in a living body, the hybridoma is given to an animal in the abdominal cavity, and the monoclonal antibodies are allowed to accumulate in the ascites, from which the monoclonal antibodies are collected. Here, it is preferable to give the animal mineral oil such as pristane prior to the administration of the antibody-producing hybridomas.

Purification of the monoclonal antibodies of this invention from the culture broth or from the ascites is performed by way of chromatography using an anion exchange column or a protein A column, or ammonium sulfate fractionation which are generally followed for the purification process of IgG.

The immunoglobulin class of the thus obtained monoclonal antibody of this invention is $IgG_1$, $\kappa$, and the antibody is specifically reactive with human myocardial C protein.

Due to the specificity of the monoclonal antibody of this invention with human myocardial C protein, the antibody is usable in the diagnosis of heart diseases: Being labelled with an enzyme, radioisotope, fluorescent substance and so on, it provides information concerning distribution of human myocardial C protein in the heart muscle and the amount of the protein flowed out into the blood circulation.

Enzymes to be used as an label include peroxidase, alkaline phosphatase and beta-galactosidase. Radioisotopes include $^{111}In$, $^{99m}Tc$, $^{67}Ga$, $^{131}I$, $^{125}I$ and $^{123}I$. Fluorescent substances include fluorescence isothiocyanate. Labelling of the monoclonal antibody of the present invention is performed according to any known method.

In the diagnosis of the heart diseases utilizing the drug according to this invention, several approaches are mentioned. In vitro approach includes various immunoassays using the labelled monoclonal antibody of the present invention, such as competitive or sandwitch enzyme immunoassay, radioimmunoassay, agglutination test and agglutination inhibition test, where the antigen is detected quantitatively or qualitatively. In the practice of the immunoassays, immunoreactions may be carried out on immobilized antibodies which are prepared by immobilizing antibodies on carrier beads made of polystyrene or the like. Meanwhile, an example of in vivo approach is that the monoclonal antibody of the present invention is labelled with any of the mentioned radioisotopes, then the radio activity is measured with a scintillation camera or the like from outside of the patient's body, thereby information concerning the region and seriousness of the myocardiopathy is obtained.

The theoretical background of the diagnosis according to the present invention is explained hereinbelow. Cell membranes play an important role in the transportation of various substances in the living body. For instance, simple diffusion of antibodies into living cells will never occur though they may be discharged out of cells. In the myocardiopathy, cell membranes of the heart muscle are broken and therefore they can no more serve as a barrier against the transportation of substances. In such situations, high-molecular proteins such as antibodies freely pass through the heart muscle cell membrane, and consequently they can intrude inside of the myocardial cells. Accordingly, when the drug for the diagnosis of heart diseases according to this invention is administered to a patient suffering from myocardiopathy, the monoclonal antibodies freely pass through the heart muscle cell membrane and bind with human myocardial C protein which is a constitutent protein of the myocardial cells. If the monoclonal antibodies are labelled with a radioisotope, scintiscanning can be performed. For instance, anti-human myocardial C protein monoclonal antibody labelled with $^{111}In$ is intravenously administered to a patient, and radioactivity is measured from the outside of the patient with a scinticamera as the time passes. By this, it is possible to observe the distribution of $^{111}In$ labelled anti-human myocardial C protein monoclonal antibody in the body non-invasively. If the patient has a suffered region in the heart muscle, the scintiscanning reveals, by the intensity of the radioactivity, the region and seriousness of the disease, thus the drug containing an anti-human myocardial C protein monoclonal antibody is very useful in the diagnosis of the heart diseases accompanied by myocardiopathy.

Further, if cell tissues of the heart muscle are destroyed due to a heart disease accompanied by myocardiopathy, myocardial cell membrane is broken and myocardial C protein, a constituent protein of the heart muscle cell tissues, flows out into the blood circulation. Based on this phenomenum, immunoassay can be performed using the monoclonal antibody of the present invention, where the amount of human myocardial C protein is measured in the peripheral blood to determine the seriousness of the heart disease accompanied by myocardiopathy and predict the prognosis. Accordingly, the anti-human myocardial C protein monoclonal antibody is also useful as a diagnosis drug to be used in vitro assays including immunoassays.

EXAMPLES

This invention will now be explained by way of examples, which however should not be construed as limiting the invention thereto.

Example 1

Preparation of Hybridomas

Human heart muscle was used as a starting material. The process described in Biochem. J. (K. M. Prince, 91, 571–580(1980)) was followed to purify the myosin. By SDS-PAGE technique, the target band of myocardial C protein was obtained. An immunogen was obtained from the gel by extraction.

Female BALB/C mouse was subcutaneously immuned with 200 micro liters (50 micro grams) of complete Freund's adjuvant mixture 4 times with an interval of 2 weeks. Three days after the last immunization, the spleen was taken out, and the spleen cells and myeloma cells (P3-X63-Ag8) were fused in the presence of polyethylene glycol. The fused cell were suspended in HAT medium and cultured. Screening of antibody-producing strains was performed on a frozen sample of the human heart muscle by indirect fluorescent antibody technique. Cloning of antibody-producing cells specific to human myocardial C protein was carried out by way of limiting dilution technique to obtain the target hybridoma (AOC-1, FERM BP-2473).

Example 2

Purification of Monoclonal Antibody

The hybridomas obtained in Example 1 were administered into the abdominal cavity of a mouse pretreated with pristane. From the ascites, antibodies were separated. Finally, monoclonal antibodies (IgG$_1$, κ) specific to human myocardial C protein were obtained. Analysis by Western-blotting method confirmed that the antibodies specifically react with human myocardial C protein.

Example 3

Specificity of Anti-human Myocardial C Protein Monoclonal Antibody Against the Human Heart Muscle A tissue slice of human old myocardial infarction, which was confirmed by hematoxiline eosine staining to have healthy myocardial cells remained was observed under fluorescent microscope by way if indirect fluorescent antibody technique using the anti-human myocardial C protein monoclonal antibody obtained in Example 2. As a result, positive reaction was observed only against human mycardinal cells.

Example 4

Specificity of Anti-human Myocardial C Protein Monoclonal Antibody to Rabbit Ischemic Myocardiopathy A healthy rabbit of Japanese white species, weighing about 2.5 kg, was put under anesthesia with 35 mg/kg of pentobarbital sodium. Thoracotomy was performed from the third intercostal space at the left chest. Coronary ramus circumflexus was ligated with suture having needle designed for the vessel suture. A rabbit having ischemic myocardiopathy was thus artificially prepared. Twenty four hours after the thoracotomy, 1 ml of 0.02M phosphate buffer solution containing 0.15M NaCl and 10 mg of anti-human myocardial C protein monoclonal antibody obtained in Example 2 was administered to the rabbit in the ear vein. Two hours after the administration, the rabbit was killed by injecting a large amount of pentobarbital sodium into the ear vein. The heart was taken out and a sample of ischemic myocardiopathy was provided by use of a safety razor. A tissue embedding agent (product of Miles Laboratories, Inc., Tissue-TEK O.C.T. 4583) was used for embedding the sample. The embedded sample was frozen in aceton added with dry ice. A tissue section having a thickness of 5 micro-meters was prepared with a frozen section making apparatus (manufactured by Leitz Co., KRYOSTAT 1720 DIGITAL), and it was fixed in cold aceton (4° C.) for 30 seconds. Anti-mouse IgG goat antibody labelled with a fluorescent dye (Fluorescence isothiocyanate, FITC) was diluted with 0.01M phosphate buffer solution containing 0.15M NaCl, and 200 micro-liters of the diluted solution was used per one section for staining for 15 minutes. The stained section was washed with an excessive volume of 0.01M phosphate buffer solution containing 0.15M NaCl, and mounted in 50% glycerol-phosphate buffer (glycerol: 0.01M phosphate buffer containing 0.15M NaCl=1:1). Observation under fluorescent microscope revealed that intense fluorescence was observed at the region of ischemic myocardiopathy which was separately confirmed by hematoxiline.eosine staining. From this, it is concluded that anti-human myocardial C protein monoclonal antibodies specifically accumulate at the region of ischemic myocardiopathy.

Example 5

Coupling of Anti-human Myocardial C Protein Monoclonal Antibody and DTPA ($C_{14}H_{23}N_3O_{10}$)

Into a silicone-coated test tube of 12 mm × 75 mm was placed 1 ml of a solution containing 0.02M phosphate buffer containing 0.15M NaCl and anti-human myocardial C protein monoclonal antibody (8.04 mg/ml) and 2.5 ml of 0.1M NaHCO$_3$, and mixed with a stirrer (3 mm φ×6 mm) made of Teflon (trademark), to which was added a solution containing cyclic DTPA anhydride ($C_{14}H_{19}N_3O_8$) and dimethylsulfoxide. Stirring was performed for one hour at room temperature. The solution was placed in a suction condensing apparatus (manufactured by Sartorius Co., Collodion Bags SM 13200). External solution of the bag was 0.01M phosphate buffer solution containing 0.15M NaCl. The condensed liquid was introduced into a dialysis tube and dialyzed with 5 liters of 0.01M phosphate buffer solution containing 0.15M NaCl. Two mililiters of 3.6 mg/ml anti-human myocardial C protein monoclonal antibody-DTPA solution was obtained. The yield of this coupling reaction was about 90%.

Example 6

Immunoreactivity Test of Anti-human Myocardial C Protein Monoclonal Antibody-DTPA A polystyrene micro-titer plate (manufactured by Corstar Co., #3590) was provided and 100 microliters of a solution containing human myocardial C protein and 0.1M glycine buffer (5 mM EDTA, pH 8.5) (1 μg/100 μl) were placed in each well, followed by being allowed to stand overnight at 4° C. The human myocardial C protein solution was removed by suction, and the wells were washed with 0.01M phosphate buffer solution containing 0.05% Tween 20 and 0.15M NaCl. 200 microliters of a blocking reagent (Block A) were added to each well. The plate was allowed to stand over 1 hour at room temperature. Washing was performed with a same phosphate buffer as mentioned, then solutions of anti-human myocardial C protein monoclonal antibody (100, 10, 1, 0.1, 0.01 and 0.001 μg/ml) or solutions of anti-human myocardial C protein monoclonal antibody—DTPA (100, 10, 1, 0.1, 0.01 and 0.001 μg/ml) were added to the wells each 100 microliters per well, followed by being allowed to stand for 1 hour at room temperature, thereby reactions between human myocardial C protein and anti-human myocardial C protein monoclonal antibody or anti-human myocardial C protein monoclonal antibody—DTPA proceeded. A same phosphate buffer solution as mentioned before was used for washing. 100 microliters of a second antibody (peroxidase-conjugated anti-mouse IgG goat antibody) was added to each well, and allowed to stand for 1 hour at room temperature. Again, a same phosphate buffer solution was used for washing. A substrate solution was prepared by dissolving ortho-phenylenediamine hydrochloride in a solution containing 0.05M sodium phosphate, 0.025M sodium citrate and 0.03% hydrogen peroxide to bring the concentration of the ortho-phenylenediamine hydrochloride to 3 mg/ml, and 200 microliters of the substrate solution was added to each well. Reaction was allowed to proceed for 30 minutes at room temperature. 50 microliters of 4N sulfuric acid were added to each well for terminating the reaction. Absorbance at 492 nm was measured for each well and activities of anti-human myocardial C protein monoclonal antibody and anti-human myocardial C protein monoclonal antibody—DTPA were compared. The results are shown in Table 1.

TABLE 1

| Sample ($\mu$g/ml) | Absorbance | |
|---|---|---|
| | Anti-human myocardial C protein monoclonal antibody | Anti-human myocardial C protein monoclonal antibody - DTPA |
| 100 | 1.616 | 1.990 |
| 10 | 2.196 | 2.155 |
| 1 | 2.049 | 1.820 |
| 0.1 | 1.361 | 0.917 |
| 0.01 | 0.355 | 0.385 |
| 0.001 | 0.126 | 0.163 |

The data revealed that there is little difference between the activities of anti-human myocardial C protein monoclonal antibody and anti-human myocardial C protein monoclonal antibody—DTPA at each protein concentration. In conclusion, DTPA coupling doesn't affect the activity.

Example 7

Labelling of Anti-human Myocardial C Protein Monoclonal Antibody—DTPA with $^{111}$In Into a 10 ml glass vial was placed 136 microliters of anti-human myocardial C protein monoclonal antibody—DTPA solution (3.6 mg/ml) prepared in Example 5, 861 microliters of 0.01M phosphate buffer containing 10% maltose and 0.15M NaCl, 1000 microliters of 0.2M citrate buffer and 20 microliters of radioactive 111-indium chloride ($^{111}$InCl$_3$) (52 MBq). After through agitation, it was allowed to stand for 2 hours. Thin layer chromatography revealed that $^{111}$In-antihuman myocardial C protein monoclonal antibody—DTPA had a labelling ratio of 100%.

Example 8

In vivo Distribution of $^{111}$In-antihuman Myocardial C Protein Monoclonal Antibody—DTPA in Rabbit Ischemic Myocardiopathy A rabbit operated to have ischemic myocardiopathy according to the procedures in Example 4 was provided, and it was administered with 0.5 ml (13 MBq, 0.125 mg) of $^{111}$In-antihuman myocardial C protein monoclonal antibody—DTPA in the ear vein. Fourty-eight hours later, a picture of the anterior imaging was taken with a gamma camera (manufactured by Aloka Co., Omega 500). Accumulation of $^{111}$In-antihuman myocardial C protein monoclonal antibody—DTPA in the region of ischemic myocardiopathy was confirmed. Thereafter, the rabbit was dissected to extract organs (blood, region of myocardiopathy, healthy region of heart muscle, liver, spleen, kidneys), on which radioactivity was measured with gamma counter (manufactured by Packard Co., table-top type minaxie gamma counter, Auto-Gamma 5530). The distribution data of radioactivity of each organ are shown in Table 2. In the table, "% Dose/g" means the % dose in 1 g of each organ based on the total dose of radiation.

TABLE 2

| Organs | % Dose/g | Organ/Blood |
|---|---|---|
| Blood | 0.094 | 1 |
| Ischemic myocardiopathy | 0.353 | 3.7 |
| Healthy heart muscle | 0.097 | 1.0 |
| Liver | 0.145 | 1.5 |
| Spleen | 0.195 | 2.1 |
| Kidneys | 0.272 | 2.9 |

The results confirmed that $^{111}$In-antihuman myocardial C protein monoclonal antibody—DTPA accumulated more in the region of ischemic myocardiopathy than in the region of healthy heart muscle.

Example 9

Labelling of Anti-human Myocardial C Protein Monoclonal Antibody—DTPA with $^{99m}$Tc Into a 10 ml glass vial was placed 200 microliters of anti-human myocardial C protein monoclonal antibody—DTPA solution (3.1 mg/ml) prepared in Example 5, 800 microliters of 0.1M phosphate buffer solution containing 0.15M NaCl, 50 microliters of stannous chloride solution (2 mg/ml, solution of 0.1N hydrochloric acid) and 500 microliters of $^{99m}$Tc (370 MBq), and agitated well. After allowing to stand for one hour, 50 microliters of 20% Ca-EDTA solution was added thereto. Purification was performed by the use of Sephadex G-25M column equilibrated with 0.01M phosphate buffer. The first peak was taken and filtered through a 0.22 micro-meter filter. The thin-layer chromatography analysis revealed that $^{99m}$Tc-antihuman myocardial C protein monoclonal antibody—DTPA had a 90% labelling ratio.

Example 10

In vivo Distribution of $^{99m}$Tc-antihuman Myocardial C Protein Monoclonal Antibody—DTPA in Rabbit Ischemic Myocardiopathy The general procedures of Example 4 was followed to prepare an ischemic myocardiopathy rabbit. One mililiter (37 MBq) of $^{99m}$Tc-antihuman myocardial C protein monoclonal antibody—DTPA was administered in the ear vein. Two and a half hours later, a picture of the front body was taken with a gamma camera (manufactured by Aloka Co., Omega 500). Accumulation of $^{99m}$Tc-antihuman myocardial C protein monoclonal antibody—DTPA in the region of ischemic myocardiopathy was confirmed. Radioactivity distribution data were obtained in organs as described in Example 8. The results are shown in Table 3.

TABLE 3

| Organs | % Dose/g | Organ/Blood |
|---|---|---|
| Blood | 0.051 | 1 |
| Ischemic myocardiopathy | 0.151 | 3.0 |
| Healthy heart muscle | 0.039 | 0.8 |
| Liver | 0.351 | 6.9 |
| Spleen | 0.161 | 3.3 |
| Kidneys | 0.171 | 3.4 |

From the data, it is confirmed that $^{99m}$Tc-antihuman C protein monoclonal antibody—DTPA accumulated more in the region of ischemic myocardiopathy than in the region of healthy heart muscle.

What is claimed is:

1. An anti-human myocardial C protein monoclonal antibody which is obtained from hybridoma AOC-1 (FERM BP-2473), wherein the antibody specifically binds to human myocardial C protein.

2. The anti-human myocardial C protein monoclonal antibody according to claim 1, wherein the immunoglobulin class of said antibody is IgG$_1$, κ.

3. Hybridoma AOC-1 (FERM BP-2473).

4. A composition for the diagnosis of heart diseases in humans which comprises an anti-human myocardial C protein monoclonal antibody according to claim 1 labelled with an enzyme, radioisotope or a fluorescent substance.

5. A composition according to claim 4, wherein the antibody is labelled with a radioisotope which is $^{111}$In, $^{99m}$Tc, $^{67}$Ga, $^{131}$I, $^{125}$I or $^{123}$I.

* * * * *